United States Patent [19]

Dewey et al.

[11] 4,264,607
[45] Apr. 28, 1981

[54] A40A EFROTOMYCIN-LIKE ANTIBIOTIC IN FERMENTATION BROTH

[75] Inventors: Ray S. Dewey, Martinsville; Vincent P. Gullo, Edison; Sheldon B. Zimmerman, Springfield, all of N.J.; Satoshi Omura, Tokyo; Ruiko Oiwa, Yokohama, both of Japan

[73] Assignee: Merck & Co., Inc., Rahway, N.J.

[21] Appl. No.: 74,202

[22] Filed: Sep. 13, 1979

Related U.S. Application Data

[63] Continuation-in-part of Ser. No. 955,553, Oct. 27, 1978, abandoned.

[51] Int. Cl.³ .............................................. A61K 31/44
[52] U.S. Cl. .................................. 424/263; 435/899; 542/421
[58] Field of Search ...................... 542/421; 424/263; 435/118, 899

[56] References Cited

U.S. PATENT DOCUMENTS

| | | | |
|---|---|---|---|
| 3,864,334 | 2/1975 | Pallos | 424/263 X |
| 3,884,941 | 5/1975 | Karrer | 542/421 X |
| 3,928,616 | 12/1975 | Pallos | 424/263 |
| 4,024,251 | 5/1977 | Maiese et al. | 536/17 X |
| 4,110,532 | 8/1978 | Johnson et al. | 542/421 X |

*Primary Examiner*—Robert J. Warden
*Attorney, Agent, or Firm*—Frank M. Mahon; Julian S. Levitt

[57] ABSTRACT

There is disclosed a new antibiotic agent, A40A, produced by *Streptomyces lavedulae* MA-4758 (ATCC 31312) under suitable conditions. Said antibiotic shows antibacterial and growth-permittant activity.

6 Claims, 2 Drawing Figures

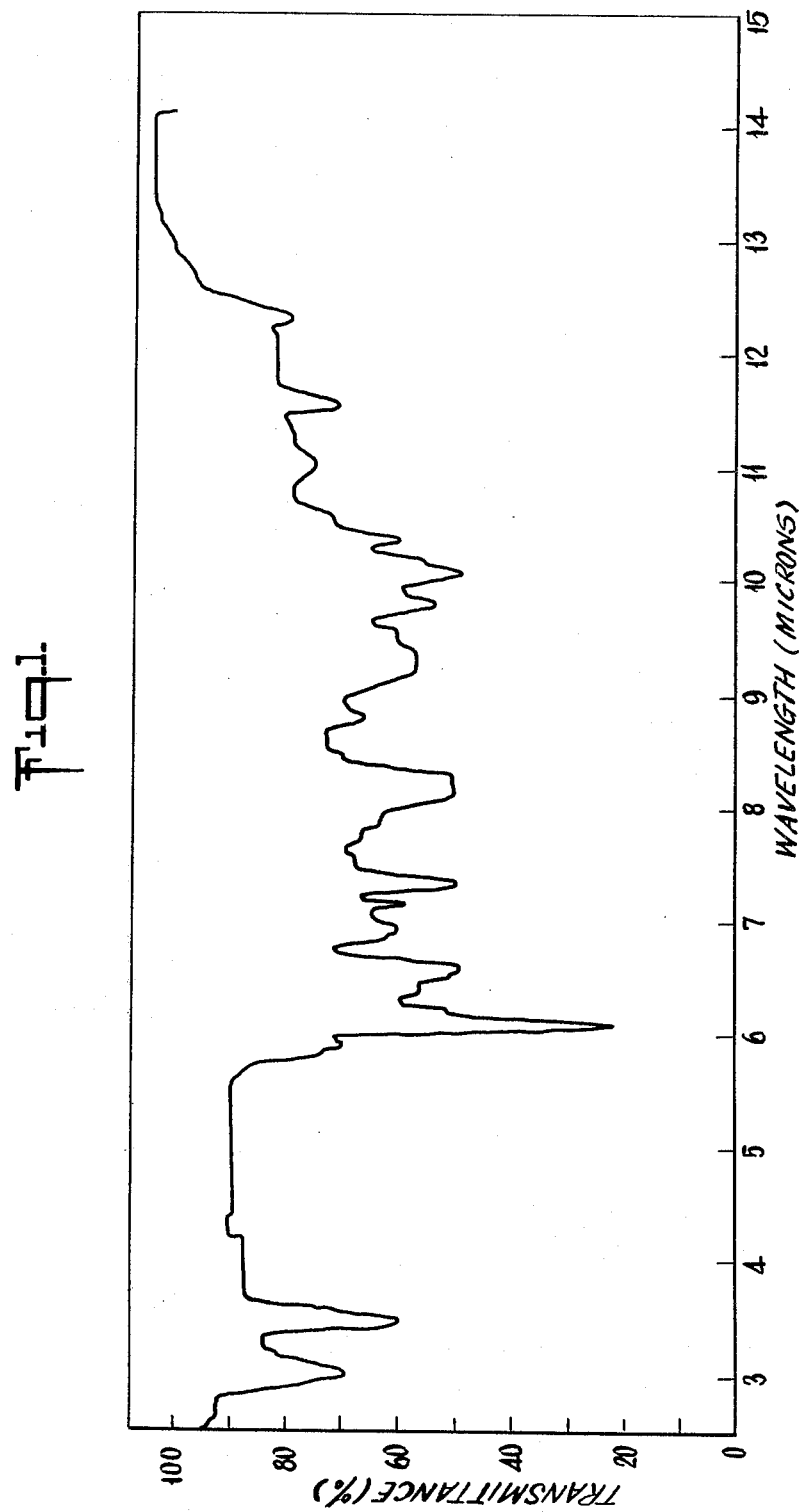

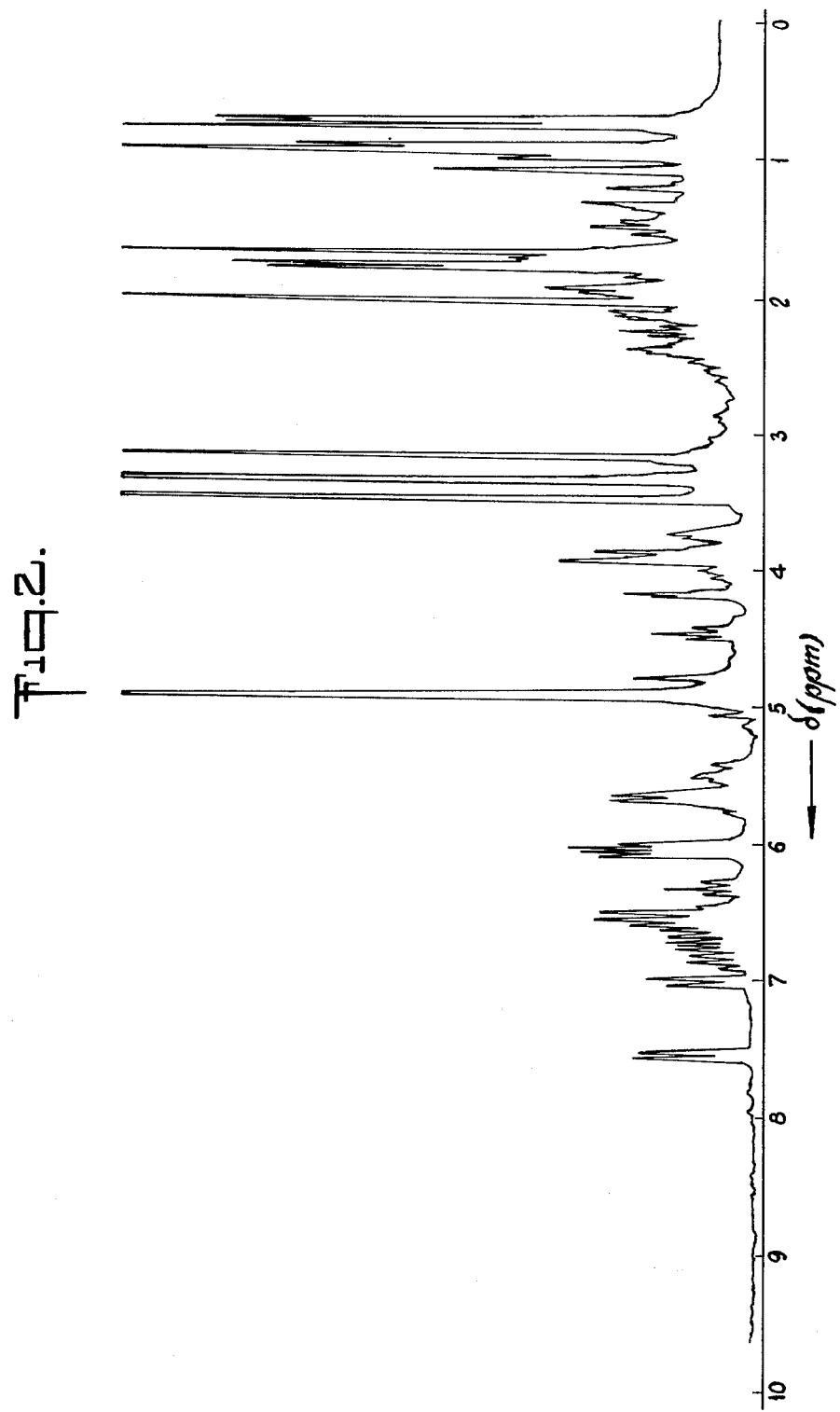

A40A EFROTOMYCIN-LIKE ANTIBIOTIC IN FERMENTATION BROTH

SUMMARY OF THE INVENTION

This application is a Continuation-in-part of prior co-pending application Ser. No. 955,553 filed Oct. 27, 1978 now abandoned.

This invention relates to a new antibiotic agent A40A with antibacterial activity, growth permittant activity and to a method for its production. The antibiotic is produced by growing *Streptomyces lavendulae* MA-4758 (ATCC 31312) in an aqueous nutrient medium comprising assimilable carbon and assimilable nitrogen sources under submerged aerobic conditions until substantial antibiotic is imparted to the medium.

The antibiotic is recovered from the fermentation medium by filtering off the mycelium. The filtrate is adsorbed and eluted on the appropriate resin. Further purification is effected by evaporation, extraction, precipitation and/or chromatography to yield substantially pure A40A.

A40A is an antibiotic which is effective against gram-positive and selected gram-negative bacteria and may be used to treat infections in animals. Furthermore, A40A can be used as a growth-permitting agent for animals such as chickens and pigs.

DESCRIPTION OF THE INVENTION

This invention relates to the production by fermentation and isolation of a useful antibiotic substance. More particularly, this invention relates to the preparation of antibiotic A40A by cultivating *Streptomyces lavendulae* under controlled conditions, followed by isolation of said antibiotic.

The antibiotic A40A is obtained by growing under controlled conditions the microorganism, *Streptomyces lavendulae*, in a fermentation broth. The fermentation may be carried out in media containing suspended nutrient matter or predominantly clear media wherein the media is substantially free of suspended nutrient matter.

Based upon extensive taxonomic studies, *Streptomyces lavendulae* was identified as an actinomycete and has been designated MA-4758 in the culture collection of MERCK & CO., Inc., Rahway, New Jersey. A culture thereof has been placed on permanent deposit with the culture collection of the American Type Culture Collection, 12301 Parklawn Drive, Rockville, Maryland 20852 and assigned accession No. ATCC 31312.

The classification keys for the genus Streptomyces and the culture descriptions of Streptomyces species found in Bergey's *Manual of Determinative Bacteriology* (8th Edition, 1974, Williams and Wilkins and *International Journal of Systematic Bacteriology*, 18, 138 (1968) were searched for a Streptomyces species having morphological and cultural characteristics similar to those of MA-4758. In these afore-mentioned classical references, the *Streptomyces lavendulae* shows morphological and close cultural characteristics with the A40A-roducing culture MA-4758. Therefore, MA-4758 is designated *Streptomyces lavendulae*.

The morphological and cultural characteristics of *Streptomyces lavendulae* MA-4758 are set forth in the following table.

Morphology:

Sporophores are long, branching structures with long flexuous spore chains, some ending in loose coils and many ending in tight spirals. Spores are oval to cylindrical, $0.9\mu \times 1.2\mu$. Spores have smooth surface as seen by electron microscope. (V=vegetative growth; A=aerial mycelium; SP=soluble pigment).

Oatmeal agar (ISP Medium 3)
 V: Reverse—reddish brown;
 A: Powdery, light rose-beige (4ec) with lavender tinge, mixed with white;
 SP: Light rose-brown.
Czapek Dox agar (sucrose nitrate agar)
 V: Flat, spreading, white to pale cream;
 A: Poor, white with beige cast;
 SP: None.
Egg albumin agar
 V: Flat, spreading, white to pale cream;
 A: Sparse, white with pinkish beige cast;
 SP: None.
Glycerol asparagine agar (ISP Medium 5)
 V: Reverse—dark rose-brown;
 A: Powdery, pale rose-beige;
 SP: Rose-brown.
Inorganic salts-starch agar (ISP Medium 4)
 V: Reverse—pale rose-brown;
 A: Powdery, light rose-beige (4ec);
 SP: Very pale rose-tan.
Yeast extract-dextrose+salts agar
 V: Reverse—reddish brown;
 A: Powdery, dark rose-beige (5ec) edged with light rose-beige (4ec) mixed with white;
 SP: Rose-brown.
Yeast extract-malt extract agar (ISP Medium 2)
 V: Reverse—reddish brown;
 A: Powdery, dark rose-beige (5ec) edged with light rose-beige (4ec), lavender tinge, mixed with white;
 SP: Rose-brown.
Peptone-iron-yeast extract agar
 V: Brown;
 A: None;
 SP: Dark brown;
 Melanin: Positive.
Nutrient agar
 V: Tan;
 A: Sparse, beige;
 SP: Light rose-brown.
Nutrient starch agar
 V: Tan;
 A: Sparse, light beige;
 SP: Light reddish-brown;
 Hydrolysis of starch: Good.
Nutrient gelatin agar
 V: Tan;
 A: Sparse, beige;
 SP: Light rose-brown;
 Liquefaction of gelatin: Good.
Gelatin stabs
 V: Tan;
 A: None;
 SP: Greenish-brown;
 Liquefaction of gelatin: Complete.
Skim milk agar
 V: Tan;
 A: None;
 SP: Light rose-brown;
 Hydrolysis of casein: Good.
Litmus milk
 V: Tan growth ring;
 A: None;
 Color: Purple;

Coagulation and/or peptonization: Peptonization, becoming alkaline.
Potato plug
V: Dark brown;
A: None;
SP: Some browning of medium.
Loeffler's Blood serum
V: Brown;
A: None;
SP: Browning of medium;
Liquefaction: Moderate.
Nutrient tyrosine agar
V: Brown;
A: Light beige;
SP: Light brown;
Decomposition of tyrosine: Positive.
Carbon utilization
Pridham-Gottlieb basal medium+1% carbon source;
+ =growth; ± =growth poor or questionable;
− =no growth as compared to negative control (no carbon source).
Glucose+
Arabinose−
Cellulose−
Fructose−
Inositol−
Lactose−
Maltose+
Mannitol−
Mannose−
Raffinose−
Rhamnose−
Sucrose±
Xylose−
Temperature range (Yeast extract-dextrose+salts agar):
28° C.—Good growth—both vegetative and aerial mycelia;
37° C.—Good growth—both vegetative and aerial mycelia;
50° C.—No growth.
Oxygen requirement (Stab culture in yeast extract-dextrose+salts agar):
Aerobic.

All readings taken after three weeks at 28° C. unless noted otherwise. pH of all media approximately neutral (6.8–7.2).

Color number designations taken from *Color Harmony Manual*, 1958, 4th Edition, Container Corporation of America, Chicago, Illinois.

In the case wherein the fermentation is carried out in media containing suspended nutrient matter the antibiotic is found mainly in the filtered broth. The antibiotic is isolated from the filtered broth by adsorbing the antibiotic on the appropriate resin and eluting.

In media containing no suspended nutrient matter, most of the A40A is found in the predominantly clear fermentation broth.

A preferred method for obtaining the antibiotic of this invention is by growing, under controlled conditions, the microorganism, *Streptomyces lavendulae* MA-4758 in a medium containing suspended nutrient matter or in a clear medium substantially free of suspended nutrient matter and adsorbing the filtered broth on the appropriate resin and eluting. The eluate is concentrated. The concentrate is extracted by adjusting to acid pH and adding a water immiscible organic solvent. The solvent layer is drawn off and evaporated in vacuo. The residue is redissolved in an appropriate polar organic solvent such as ethylacetate and added dropwise to a nonpolar organic solvent such as hexane. The precipitate formed is chromatographed over silica gel to yield the antibiotic A40A.

In the process described above wherein extraction is carried out with water immiscible polar organic solvents, representative examples of said solvents include N-butanol alkyl esters of lower alkanoic acids such as methyl formate, ethyl formate, methyl acetate, ethyl acetate, n-butyl acetate, isobutyl acetate, ethyl propionate; a ketone such as cyclohexanone or methyl ethyl ketone; or a halogenated lower hydrocarbon such as chloroform, methylene chloride, carbon tetrachloride, ethylene dichloride, 1-chloro-2,2-dimethylpropane, tetrachloroethylene, or bromoform.

The antibiotic A40A isolated from the fermentation broth is subjected to purification by adsorption and chromatography over surface active adsorbing agents. A suitable surface active adsorbing agent is a hydrophobic non-ionic macro porous copolymer of polystyrene cross-linked with divinylbenzene known by the Rohm and Haas trade names Amberlite XAD-1 to XAD-12. A preferred resin for purifying A40A is XAD-2. Suitable solvents for eluting adsorbed A40A aqueous organic solvent solutions of acetone and lower alkanols e.g. aqueous solutions of methanol, ethanol, isopropanol, butanol and the like. The preferred solvent for eluting A40A from XAD-2 resin is 75% acetone:water. For further purification, silica gel is a suitable surface active adsorbing agent.

*Streptomyces lavendulae* MA-4758 is simply illustrative of the type of strain of microorganism which can be used in the production of A40A and it should be understood that the present invention is not limited to organisms meeting these particular descriptions. This invention includes the use of the other microorganisms, including strains of actinomycetes either isolated from nature or obtained by mutation as, for example, those obtained by natural selection or those produced by mutating agents, for example, X-ray irradiation, ultraviolet irradiation, nitrogen mustards and the like which, under suitable conditions will yield A40A.

A40A is produced during the aerobic fermentation of suitable aqueous nutrient media under controlled conditions via the inoculation with the organism *Streptomyces lavendulae* MA-4758. Aqueous media, such as those employed for the production of other antibiotics are suitable for producing the antibiotic A40A. Such media contain sources of carbon, nitrogen and inorganic salts assimilable by the microorganism. The choice of media is not critical and the fermentation may be carried out in media containing suspended nutrient matter or predominantly clear media wherein the media is substantially free of suspended nutrient matter.

In general, carbohydrates such as sugars, for example dextrose, glucose, arabinose, maltose, raffinose, xylose, mannitol and the like and starches such as grains, for example, oats, rye, corn starch, corn meal, potato and the like can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, nutrient broth, yeast extract, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.2% to 6% by weight of the aqueous medium.

Media described in the Examples are merely illustrative of the wide variety of media which may be employed, and are not intended to be limitative.

The fermentation is carried out at temperatures ranging from about 20° C. to 37° C.; however, for optimum results it is preferable to conduct the fermentation at temperatures of from about 24° C. to 32° C. The pH of the nutrient media suitable for growing the *Streptomyces lavendulae* MA-4758 culture and producing the antibiotic A40A should be in the range of from about 6.0 to 8.0.

A small scale fermentation of the antibiotic is conveniently carried out by inoculating a suitable nutrient medium with the antibiotic-producing culture and, after transfer to a production medium, permitting the fermentation to proceed at a constant temperature of about 28° C. on a shaker for several days. At the end of the incubation period, the fermentation broth can be filtered and the antibiotic adsorbed and eluted from the appropriate resin.

The small scale fermentation is conducted in a sterilized flask via a one-, two-, three- or four-stage seed development. The nutrient medium for the seed stage may be any suitable combination of carbon and nitrogen sources. The seed flask is shaken in a constant temperature chamber at about 28° C. for a period of from one to two days and some of the resulting growth is used to inoculate either a second stage seed or the production medium. Intermediate stage seed flasks, when used, are developed in essentially the same manner; that is, part of the contents of the flask are used to inoculate the production medium. The inoculated flasks are shaken at a constant temperature for several days and at the end of the incubation period of antibiotic A40A is isolated as already described.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of several days as, for example, from two to four days while agitating and/or aerating the nutrient medium and maintaining the temperature at about 28° C. The yield of A40A is generally between 20 mg. to 200 mg. per liter of production broth as determined by bioassay.

Physical Properties

Antibiotiic A40A is slightly deliquescent amorphous yellow substance which analyzes as $C_{44}H_{62}N_2O_{10}$. The mass spectrum of the trimethylsilyl derivative exhibited peaks up to m/e 1210 which corresponded to $C_{44}H_{62}N_2O_{10} + 6 (CH_3)_3Si - 6H$. The combustion analysis gave C, 65.32; H, 7.92; N, 3.14. Calcd. for $C_{44}H_{62}N_2O_{10} \cdot 2H_2O$: C, 65.00; H, 7.69; N, 3.52.

The compound exhibited the following spectral properties. Its ultraviolet spectrum showed maxima at $\lambda = 355$ nm, E% 420 and at $\lambda = 231$ nm, E% 648 in methanol. It showed a rotation of $\alpha_D^{25} = 81.6°$ for a 1% solution in methanol. The infrared spectrum of a chloroform solution was recorded on a Perkin Elmer infrared spectrometer Model 137 and is exhibited in FIG. 1. The hydrogen NMR spectrum was recorded on a perdeuteromethanol solution of the antibiotic on a Varian Nuclear Magnetic Resonance Spectrometer Model SC 300 and is shown in FIG. 2. The peak positions on the abscissa are indicated in the δ scale for which in the present case the peak for the residual protic methyl group of methanol is referenced at 3.33 parts per million downfield from tetramethylsilane.

The 13C nuclear magnetic resonance spectrum A40A exhibited the peaks listed in Table 1. The spectrum was recorded on a methanol solution with tetramethylsilane or an internal standard using a Varian Nuclear Magnetic Spectrometer Model CFT 20. The peak positions are given in parts per million downfield from tetramethylsilane.

Table 1

Line Positions in the 13C NMR Spectrum of A40A 9.81, 11.16, 11.91, 12.38 (2C), 13.58, 21.49, 23.00, 36.49, 37.04, 38.21, 40.17, 42.07, 56.28, 58.24, 69.23, 72.59, 73.69, 77.47, 89.98, 99.38, 109.46, 113.06, 126.40, 127.83, 128.24, 130.24, (5±1 C), 132.17, 132.63, 135.03, 135.50, 136.85 (2C), 138.94, (1−2C), 140.41, 141.29, 164.61, 176.64, 177.92, 202.34.

The above data were obtained on the main component of A40A. The biological data were obtained on material which was 60% pure by ultraviolet spectra and thin layer chromatography assay. The antibiotic also exhibited faint spots by thin layer chromatography attributed to small amounts of interconvertible isomers which has been a feature characteristic to this class of compounds.

The structure of antibiotic A40A is the following:

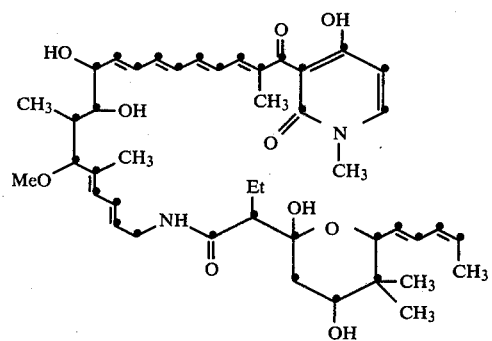

In the above structure, the pyran has the following configuration at its asymmetric centers: S at the hemiketal 2, S at the hydroxy carbon 4, and S at the pentadienyl side chain bearing carbon 6.

Assay Procedure for Antibiotic Activity

Assays are run by the disc-plate procedure using ⅜ inch filter paper discs. The assay plates are prepared using Difco brain heart infusion agar, buffered at pH 6.0, at 10 ml. of agar per plate. A spore suspension of the assay organism, *Bacillus circulans* (MB 264) is diluted in sterile saline solution to a suspension having 45% transmittance at a wave length of 660 mµ. This suspension is added at 33.3 ml./liter of agar medium prior to pouring the plates.

The assay plates are held at 4° C. until used (5 day maximum). Following the application of the antibiotic-saturated assay discs the plates are incubated at 28° C. for a period of from 16 to 24 hours. Zones of inhibition are read as mm. diameter. They are used to determine relative potencies or, when compared with a purified reference standard, the potency in µg./ml. Assays of A40A in fermentation broths, mycelia and suspended nutrient matter separated from fermentation broths and in broths free of solids are performed after extracting the A40A into a suitable solvent. Assays on solutions containing A40A, 200 µg./ml. using ⅜ inch discs show 16 mm. zones of inhibition. When such an assay is performed in a quantitative fashion, from 100 to 200 µg./ml. of antibiotic can be detected.

A40A shows activity against gram-positive bacteria, but only limited activity against gram-negative bacteria. In vitro, A40A is effective against *Sarcina lutea* (ATCC 9341), *Streptococcus faecium* (MB 2820) and *Streptococcus agalactiae* (MB 2875). Activity is also found against *Vibrio percolans* (ATCC 8461), *Klebsiella pneumoniae* (MB 1264), *Xanthomonas vesicatoria* (MB 815), *Bacillus subtilis* (ATCC 6633) and *Alcaligenes faecalis* (ATCC 213).

A40A is useful both as an antibiotic and as a growth-permittant agent in animals.

When A40A is used as an antibiotic, the specific means employed for administering it to the animal is critical, and only some of the methods now used or available for treating infected animals or animals susceptible to infection are satisfactory.

A40A can be used as an antibiotic, for example, in the form of pharmaceutical preparations which contain it in admixture or conjunction with an organic or inorganic, solid or liquid non-toxic pharmaceutical excipient suitable for enteral, parenteral or local administration. Suitable excipients are substances that do not react with the antibiotic, for example, water, gelatin, lactose, starches, stearyl alcohol, magnesium stearate, talcum, vegetable oils, benzyl alcohols, gums, propyleneglycol, polyalkyleneglycols, white petroleum jelly, cholesterol or other known medicinal excipients. The pharmaceutical preparations may be, for example, tablets, dragees, ointments, creams or capsules, or in liquid form solutions, suspensions or emulsions. They may be sterilized and/or contain assistants, such as preserving, stabilizing, wetting or emulsifying agents; solution promoters, salts for regulating the osmotic pressure or buffers.

Where it is desired to administer the antibiotic in dry, solid unit dosage form, capsules, boluses or tablets containing the desired amount of antibiotic are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of A40A depending upon factors such as the type of host animal to be treated, the severity and type of infection and the weight of the host. The antibiotic may be administered on a daily basis at from about 5 to 100 mg. per kilograms of body weight.

Included in this invention are the non-toxic, pharmaceutically acceptable salts or esters of A40A, for example, the alkali and alkaline earth metal salts such as those derived from sodium, potassium, ammonium and calcium or salts with organic bases, for example, triethylamine, N-ethylpiperidine, dibenzylethylenediamine.

In addition to its use as an antibiotic, A40A is useful as a feed additive to permit the growth of animals such as chickens, sheep and cattle. The use of A40A shortens the time required for bringing animals up to marketable weight.

When A40A is used as a growth permittant in animals, it can be administered as a component of the feed of the animals or may be suspended in the drinking water.

When A40A is used as a component of animal feed, it is first formulated as a feed supplement. In such feed supplements, A40A is present in relatively concentrated amounts intimately dispersed in an inert carrier or diluent. The feed supplement can be added to the feed or made into a premix by an intermediate dilution or blending step. By inert carrier is meant one that will not react with the antibiotic and one that may be administered safely to animals. Preferably, the carrier is one that is, or may be, an ingredient of the animal ration. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The antibiotic is intimately dispersed throughout the carrier by methods such as grinding, stirring, milling or tumbling. Compositions containing from about 5 to 50% by weight of the antibiotic are particularly suitable as feed supplements.

Examples of typical feed supplements containing A40A dispersed in a solid carrier are:

|     |                         | lbs. |
|-----|-------------------------|------|
| (A) | A40A                    | 5    |
|     | Wheat Standard Middling | 95   |
| (B) | A40A                    | 50   |
|     | Corn distiller's grains | 50   |

These and similar feed supplements are prepared by uniformly mixing the antibiotic with the carrier.

The feed supplement can be added directly to the feed or made into a premix by an intermediate dilution or blending step with an orally ingestable carrier. Compositions containing 0.03% to 5% by weight of the antibiotic are particularly suitable as premixes. These premixes are prepared by uniformly mixing the antibiotic with an orally ingestable carrier.

Such supplements or premixes are added to the animal feed in an amount to give the finished feed the concentration of A40A desired for growth permittant. In chickens, A40A is fed at a final concentration of between 10–100 ppm per ton of feed in order to achieve the desired growth permitting result. In the case of swine, including swine infected with *Mycoplasma hyorhinis,* (PPLO) A40A may be administered in the feed at similar levels.

In the above discussion of this invention, emphasis has been placed on solid compositions wherein the A40A is mixed with an edible carrier in a feed supplement, in a so-called premix or in the final feedstuff. This is the preferred method of administering the A40A. An alternate method is to suspend the A40A in the drinking water of the animals. The quantity that may be suspended in the water without undue settling is limited. Emulsifiers or surface-active agents may be employed for this latter purpose.

It will likewise be understood by those skilled in this art that special feed supplement formulations and finished animal feeds containing A40A may also include vitamins, other antibiotics and growth-permitting agents and other nutritional substances.

A40A is useful against poultry PPLO at a range of 5 to 100 mg./kg. A preferred range for a single dose is from 35 to 45 mg./kg. For reasons of convenience a preferred method of administering the antibiotic in the treatment of PPLO is to admix the A40A with the animal feed. A preferred range for PPLO is from 0.0055% to 0.02% by weight of feed.

In the treatment of air sacculitis in broilers, the $ED_{50}$ is 40 to 100 mg./kg. Accordingly, a useful dosage of A40A may vary from 10 to 150 mg./kg.

A solution of suspension for subcutaneous injection for treatment of air sacculitis in broilers may be prepared as follows:

Subcutaneous Suspension Containing 20 mg. of A40A Ampoule

A40A—20 mg.
Diluent: Sterile water for injection—2 cc.

The examples which follow illustrate methods by which the product of this invention may be obtained. The claimed process is capable of wide variation and modification and, therefore, any minor departure therefrom or extension thereof is considered as being within the skill of the artisan and as falling within the scope of this invention.

EXAMPLE 1

Shake Flask Fermentation

A portion of the slant culture containing MA-4758 having the following composition:
Peptone—5.0 g.
Glucose—10.0 g.
Meat extract—5.0 g.
NaCl—3.0 g.
Agar—15.0 g.
Distilled Water—1000 ml.
pH 7.0
is used to inoculate a baffled, 250-ml. Erlenmeyer flask containing 50 ml. of Medium A having the following composition:

Medium A

Soluble Starch—10.0 g./l.
Ardamine pH—5.0 g./l.
NZ Amine E—5.0 g./l.
Beef Extract—3.0 g./l.
$CaCO_3$—0.5 g./l.
$MgSO_4.7H_2O$—0.05 g./l.
Cerelose—1.0 g./l.
$KH_2PO_4$—0.182 g./l.
$Na_2HPO_4$—0.190 g./l.
Distilled Water—1000 ml.
pH 7.0–7.2

The above flask is shaken at 27°–28° C. on a 220 rpm shaker (2-inch throw) for three days. The growth from this seed flask is used to inoculate a 250-ml. Erlenmeyer flask containing 40 ml. of Medium B using 2 ml./flask of (5%) inoculum.

Medium B

Tomato Paste—20.0 g./l.
CPC Industrial Starch Modified—20.0 g./l.
Primary Yeast—10.0 g./l.
$CoCl_2.6H_2O$—0.005 g./l.
Distilled Water—1000 ml.
pH 7.2–7.4

This flask containing Medium B is shaken at 27°–28° C. on a 220 rpm shaker (2-inch throw) for three days and submitted for assay. Assay shows in vitro antibacterial spectrum was positive as indicated in the above text.

EXAMPLE 2

Production of Antibiotic A40A

To a slant of culture containing MA-4758 having the following composition:
Glycerol—10.0 g.
Asparagine—1.0 g.
NZ Amine E—0.5 g.
Yeast extract—0.5 g.
$K_2HPO_4$—1.0 g.
Thiamine—1.0 mg.
Agar—17.0 g.
Distilled Water—1000 ml.
pH 7.2
is added 10 ml. of Medium A having the following composition.

Medium A

Soluble Starch—10.0 g./l.
Ardamine pH—5.0 g./l.
NZ Amine E—5.0 g./l.
Beef Extract—3.0 g./l.
$CaCO_3$—0.5 g./l.
$MgSO_4.7H_2O$—0.05 g./l.
Cerelose—1.0 g./l.
$KH_2PO_4$—0.182 g./l.
$Na_2HPO_4$—0.190 g./l.
Distilled Water—1000 ml.
pH 7.0–7.2

The growth from the slant is scraped into suspension and used to inoculate a 250-ml. baffled Erlenmeyer flask containing 50 ml. of Medium A. The flask is incubated at 28° C. for 24 hours while being shaken on a 150 rpm rotary shaker.

After 24 hours, a 10-ml. sample from the above flask is added to a 2-liter baffled Erlenmeyer flask containing 500 ml. of Medium A. The 2-liter flask is incubated at 28° C. for 24 hours on a 150 rpm rotary shaker.

After 24 hours, 500 ml. of the broth from the 2-liter flask is added to a 189-liter stainless steel fermentor containing 160 liters of Medium C having the following composition.

| Medium C | |
| --- | --- |
| Dextrose | 1.0 g./l. |
| CPC Modified Starch | 10.0 g./l. |
| Meat Extract | 3.0 g./l. |
| Ardamine - Type pH | 5.0 g./l. |
| NZ Amine - Type E | 5.0 g./l. |
| $MgSO_4 . 7H_2O$ | 0.05 g./l. |
| $KH_2PO_4$ | 0.182 g./l. |
| $Na_2HPO_4$ | 0.19 g./l. |
| $CaCO_3$ | 0.5 g./l. |
| Polyglycol 2000 | 0.31 g./l. |
| pH 7.0–7.2 before Sterilization | |

The stainless steel fermentor is operated at a temperature of 28° C. using an air flow of 3 cubic feet per minute (cfm) and an agitation rate of 150 rpm/l. for a period of 24 hours. The physiology of the broth is as follows.

| Age in Hours | 0   | 24  |
|--------------|-----|-----|
| pH           | 7.1 | 7.1 |

After 24 hours, 43 liters from the above stainless steel fermentor is added to a 756-liter stainless steel fermentor containing 467 liters of Medium D having the following composition.

| Medium D | |
|---|---|
| Tomato Paste | 20 g./l. |
| Primary Yeast NF | 10 g./l. |
| CPC Modified Starch | 20 g./l. |
| $CoCl_2 \cdot 6H_2O$ | 5.0 mg./l. |
| pH 7.2–7.4 before Sterilization | |

The fermentor is operated at a temperature of 28° C. using an air flow of 10 cfm and an agitation rate of 130 rpm/l. for a period of 120 hours. To the fermentor is added Polyglycol 2000 not exceeding 0.1%. The physiology profile is as follows.

| Age in Hours | 0   | 12  | 24  | 36  | 48  | 60  |
|--------------|-----|-----|-----|-----|-----|-----|
| pH           | 6.7 | 7.1 | 7.1 | 7.0 | 7.0 | 7.0 |
| Age in Hours | 72  | 84  | 96  | 108 | 120 |     |
| pH           | 7.1 | 7.2 | 7.1 | 7.1 | 7.4 |     |

Whole broth (16 liters) is adjusted from pH 6.7 to pH 9.0 at room temperature. The whole broth is filtered through a Buchner funnel containing a supercel precoat. The filtered broth is adsorbed onto 1 liter of XAD-2 using a 20-minute contact time (the dimensions of the column are 3.5 cm. ID×80 cm. long). The column is then washed with one column volume deionized water. Activity is eluted with 2.0 liters of 75% acetone:25 deionized water mixture. The eluate is concentrated to 625 ml in vacuo at 30° C. The pH is adjusted from pH 7.2 to 4.0 and extracted two times with 625 ml. of ethyl acetate. The extracts are combined and evaporated in vacuo at 30° C. to an oily residue. The residue is redissolved in 100 ml. of ethyl acetate, and this solution is added dropwise to 500 ml. of hexane with vigorous stirring. The yellow precipitate formed is chromatographed on preparative TLC plates (silica gel) to yield 290 mg. of A40A (E% 390 at 350 nm.).

We claim:

1. A composition comprising an antibacterially effective amount of A40A having the structure:

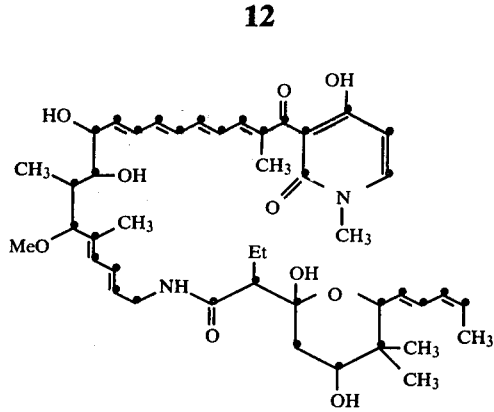

wherein the pyran has the following configuration at its asymmetric centers: S at the hemiketal 2, S at the hydroxyl bearing carbon 4, and S at the pentadienyl side chain bearing carbon 6, or its pharmaceutically acceptable salts and a non-toxic, pharmaceutically acceptable excipient.

2. A composition for use as a growth-permittant in animals comprising a growth-permitting amount of A40A having the structure:

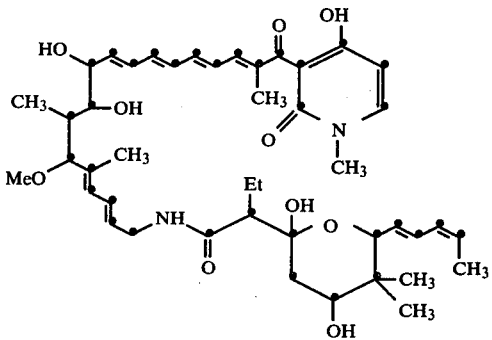

wherein the pyran has the following configuration at its asymmetric centers: S at the hemiketal 2, S at the hydroxyl bearing carbon 4, and S at the pentadienyl side chain bearing carbon 6, or its pharmaceutically acceptable salts and an inert carrier.

3. A method for preparing A40A having the structure:

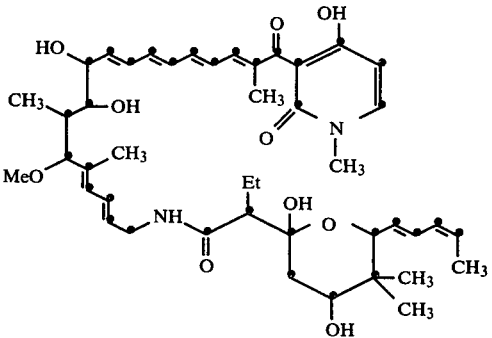

wherein the pyran has the following configuration at its asymetric centers: S at the hemiketal 2, S at the hydroxyl bearing carbon 4, and S at the pentadienyl side chain bearing carbon 6, which comprises cultivating Streptomyces lavendulae ATCC 31312 in a fermentation broth containing assimilable sources of carbohydrates, nitrogen and inorganic salts under aerobic conditions until a substantial amount of A40A is produced in the fermentation broth and recovering said antibiotic.

4. The method of claim 3 wherein the fermentation broth is filtered and the filtered broth is extracted with a water immiscible polar organic solvent.

5. The method of claim 4 wherein the extraction solvent is selected from the group consisting of methyl formate, ethyl formate, methyl acetate, ethyl acetate, N-butyl acetate, isobutyl acetate, ethyl proprionate, methyl ethyl ketone, cyclohexanone, chloroform, methylene chloride, carbon tetrachloride, ethylene dichloride, 1-chloro-2,2-dimethylpropane, tetrachloroethylene, bromoform and N-butanol.

6. A compound A40A having the following structure:

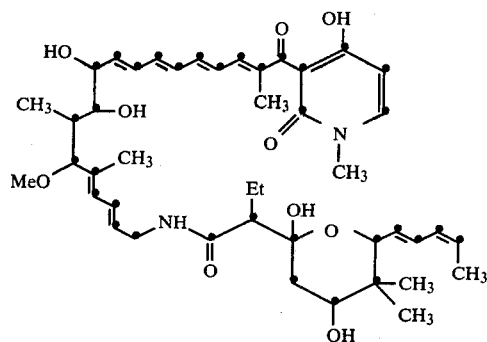

wherein the pyran has the following configuration at its asymmetric centers: S at the hemiketal 2, S at the hydroxyl bearing carbon 4, and S at the pentadienyl side chain bearing carbon 6, or its pharmaceutically acceptable salts or esters.

* * * * *